(12) United States Patent
Raveglia et al.

(10) Patent No.: US 7,662,995 B2
(45) Date of Patent: Feb. 16, 2010

(54) 1-PHENYLALKANECARBOXYLIC ACID DERIVATIVES FOR THE TREATMENT OF NEURODEGENERATIVE DISEASES

(75) Inventors: Luca Raveglia, Parma (IT); Ilaria Peretto, Parma (IT); Stefano Radaelli, Parma (IT); Bruno Pietro Imbimbo, Parma (IT); Andrea Rizzi, Parma (IT); Gino Villetti, Parma (IT)

(73) Assignee: Chiesi Farmaceutici S.p.A., Parma (IT)

( * ) Notice: Subject to any disclaimer, the term of this patent is extended or adjusted under 35 U.S.C. 154(b) by 492 days.

(21) Appl. No.: 10/546,190

(22) PCT Filed: Feb. 19, 2004

(86) PCT No.: PCT/EP2004/001596

§ 371 (c)(1),
(2), (4) Date: Oct. 10, 2006

(87) PCT Pub. No.: WO2004/074232

PCT Pub. Date: Sep. 2, 2004

(65) Prior Publication Data

US 2007/0060752 A1     Mar. 15, 2007

(30) Foreign Application Priority Data

Feb. 21, 2003  (IT) ............................ MI2003A0311
Oct. 23, 2003  (IT) ............................ MI2003A2068

(51) Int. Cl.
 *C07C 61/04*   (2006.01)
 *A61K 31/19*   (2006.01)

(52) U.S. Cl. .................. 562/499; 562/503; 562/505; 562/507; 514/572; 514/573; 546/122; 546/148; 546/176; 544/237; 544/238; 544/284; 544/333; 544/350; 544/405; 548/216; 548/335.5; 548/465

(58) Field of Classification Search ................. 546/122, 546/148, 176; 544/237, 238, 405, 333, 284, 544/350; 548/216, 465, 335.5; 562/499, 562/503, 505, 506; 514/572, 573
See application file for complete search history.

(56) References Cited

U.S. PATENT DOCUMENTS 3,746,751 A     7/1973     Noguchi et al.

FOREIGN PATENT DOCUMENTS

| JP | 49 094680 | 9/1974 |
| JP | 50 046669 | 4/1975 |
| JP | 58 177977 | 10/1983 |
| WO | WO 96/02529 | * 2/1996 |
| WO | 99/41224 | 8/1999 |

OTHER PUBLICATIONS

U.S. Appl. No. 11/572,974, filed Jan. 30, 2007, Raveglia, et al.

* cited by examiner

*Primary Examiner*—Shailendra Kumar
(74) *Attorney, Agent, or Firm*—Oblon, Spivak, McClelland, Maier & Neustadt, L.L.P.

(57) ABSTRACT

1-Phenylalkanecarboxylic acid derivatives, the processes for the preparation thereof and the use thereof in the treatment and/or prevention of neurodegenerative diseases such as Alzheimer's disease.

26 Claims, No Drawings

1-PHENYLALKANECARBOXYLIC ACID DERIVATIVES FOR THE TREATMENT OF NEURODEGENERATIVE DISEASES

CROSS REFERENCES TO RELATED APPLICATIONS

This application is a 371 of International Patent Application No. PCT/EP04/01596, filed on Feb. 19, 2004, and claims priority to Italian Patent Application No. MI2003A000311, filed on Feb. 21, 2003, and Italian Patent Application No. MI2003002068, filed on Oct. 23, 2003.

The present invention concerns 1-phenylalkanecarboxylic acids, pro-drugs and bioisosters on the carboxylic moiety thereof. The invention is also directed to a process for their preparation and the use thereof in the prevention or in the therapeutical treatment of neurodegenerative diseases, in particular Alzheimer's disease.

INTRODUCTION

Alzheimer's disease is a neurodegenerative disorder characterized by atrophy of the cerebral cortex and by a massive loss of cortical neurons and cholinergic projections of the nucleus basalis towards the cortex. From a histopathologic point of view there is a diffuse presence of extracellular and perivascular neuritic plaques and intracellular neurofibrillary tangles in the cerebral parenchyma of Alzheimer patients.

Neuritic plaques are mainly composed of aggregates of a protein with 39-43 amino acid residues known as β-amyloid (βA), and, depending on the numbers of aminoacids, $A\beta_{39}$, $A\beta_{40}$, $A\beta_{42}$ and $A\beta_{43}$.

In addition to these histopathologic lesions, there is lack in some neurotransmitters, particularly acetylcholine, serotonin, noradrenalin, dopamine, glutamate and substance P. The pharmacological approaches aimed at increasing acetylcholine cerebral levels, mainly through acetylcholine-esterase inhibitors, attained poor results from the clinical standpoint, or anyhow results which cannot significantly prevent the progress of the disease. For this reason, in recent years interest has been focused on the mechanisms of formation of the main pathologic lesions in the brain of the patients, namely both neuritic plaques and neurofibrillary tangles, and more effective therapeutical approaches have been looked for.

PRIOR ART

Epidemiological studies evidenced that chronic administration of non steroid anti-inflammatory drugs (NSAIDs) significantly decreases the onset of Alzheimer's disease in the population regularly taking these drugs. The mechanism underlying such NSAID preventive action has not been fully elucidated yet, but is apparently connected with their ability of inhibiting cyclooxygenase (COX) enzymes.

More recently, a novel pharmacological action of some non steroid anti-inflammatory drugs (NSAIDs) has been described: indomethacin, sulindac, ibuprofen and flurbiprofen can selectively reduce the production of the most neurotoxic isoform of β-amyloid peptide in cell cultures, namely the form containing 42 amino acids ($A\beta_{42}$), thus favouring the release of a less harmful isoform, $A\beta_{38}$ (Weggen et al., Nature 2001; 414 (6860): 212-6). However, the inhibition of the production of $A\beta_{42}$, which can be ascribed to the interaction of these drugs with γ-secretase (a macromolecular/multiprotein enzymatic complex with aspartyl-protease activity) has been observed in vitro at very high concentrations. Plasma and cerebral levels corresponding to the dosages used in the in vitro experimentation could significantly increase in treated patients the risk of side effects typical of COX inhibitors, such as gastrointestinal bleeding and perforating ulcers.

WO 01/78721 claims a method of preventing, delaying or reversing the progression of Alzheimer's disease by administering an $A\beta_{42}$ lowering agent, under conditions in which levels of $A\beta_{38}$ are increased and levels of $A\beta_{42}$ are left unchanged. Furthermore, methods and materials for identifying and developing $A\beta_{42}$ lowering agents and methods for identifying agents that increase the risk of developing, or hasten progression of, Alzheimer's disease, are disclosed. The examples concern indomethacin and flufenamic acid derivatives, but no examples concerning flurbiprofen derivatives are reported.

Jantzen et al, *J Neurosci* 2002; 22: 2246-2254, described a flurbiprofen derivative capable of releasing nitric oxide. The paper generically states that flurbiprofen derivatives are apparently more efficacious than other NSAIDs in clearing β-amyloid deposits, but no mention concerning any $A\beta_{42}$ lowering selective activity is made.

In this therapeutical scenario, and in the light of the potential problems of conventional NSAIDs, novel derivatives having more selective and more potent inhibitory activity on the peptide $A\beta_{42}$ while inhibiting to a lesser extent, or not inhibiting at all, cyclooxygenase would be a significant improvement in therapies aimed at preventing the onset of Alzheimer's disease and/or at delaying the cognitive decline that represent an early stage disease.

Substituted 1-phenyl-2,2-dialkyl carboxylic derivatives were described as anti-inflammatory, analgesic and antipyretic agents in GB 1,198,212, U.S. Pat. No. 3,978,071, U.S. Pat. No. 757,136, GB 1,352,723, JP49100089 and JP 50046669.

3-Halo-4-alkyl- or cycloalkyl-substituted 1-phenylcycloalkanecarboxylic derivatives were described in JP-4,7047, 375 and FR-2,012,285, as substances with the same activity.

In the paper from Kuzuna S et al (Takeda Kenkyushoho 1975, 34, 467-473) dealing with a structure-activity study of a series of phenylacetic derivatives, it is generically stated that the introduction of a cyclopropane group at the position of α carbon atom decreases the anti-inflammatory and analgesic activities.

In WO 99/41224 novel biaryl-acetic acid derivatives with anti-inflammatory activity as cyclooxygenase-2 inhibitors, useful for the treatment of a number of diseases, including Alzheimer's disease, are claimed.

SUMMARY OF THE INVENTION

The present invention concerns 1-phenylalkanecarboxylic acids, their pro-drugs, and bioisosters on the carboxylic moiety, the process for the preparation thereof, pharmaceutical compositions containing them and the use thereof in the prevention or therapeutical treatment of neurodegenerative diseases, in particular Alzheimer's disease.

The compounds of the invention inhibit the release of $A\beta_{42}$ peptide thereby being able to modulate gamma-secretase activity without affecting other important metabolic processes.

DETAILED DESCRIPTION OF THE INVENTION

The present invention is directed to compounds of general formula (I):

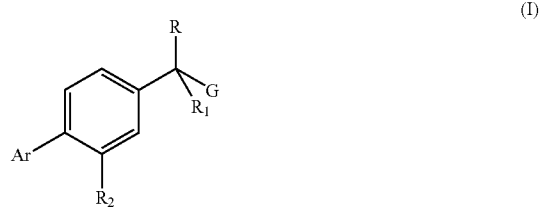

wherein:

R and $R_1$ are the same and are selected from the group of linear or branched $C_1$-$C_4$ alkyl;

otherwise they form a 3 to 6 carbon atoms ring with the carbon atom to which they are linked;

G is:
a COOR" group wherein R" is H, linear or branched $C_1$-$C_4$ alkyl, $C_3$-$C_6$ cycloalkyl or ascorbyl;
a $CONH_2$ or a $CONHSO_2R'''$ group wherein R''' is linear or branched $C_1$-$C_4$ alkyl or $C_3$-$C_6$ cycloalkyl;
a tetrazolyl residue;
$R_2$ is H, $CF_3$, $OCF_3$ or a halogen selected from the group of F, Cl, Br, I, preferably fluorine.
Ar is a group of formula

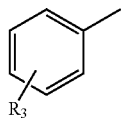

wherein $R_3$ represents one or more groups independently selected from:
halogen as previously defined;
$CF_3$;
$C_3$-$C_8$ cycloalkyl optionally substituted with one or more $C_1$-$C_4$ alkyl and/or oxo groups;
$CH=CH_2$;
CN;
$CH_2OH$;
methylendioxy or ethylendioxy;
$NO_2$
phenyl optionally substituted with one or more of the following groups: halogen; $CF_3$; $OCF_3$; OH; linear or branched $C_1$-$C_4$ alkyl; a saturated eterocycle with at least 4 carbon atoms and at least 1 heteroatom; $C_3$-$C_8$ cycloalkyl in turn optionally substituted with one or more of the following groups linear or branched $C_1$-$C_4$ alkyl, $CF_3$ or OH;
$OR_4$ or $NHCOR_4$ wherein $R_4$ is $CF_3$, linear or branched $C_2$-$C_6$ alkenyl or alkynyl; benzyl; phenyl optionally substituted with one or more of the following groups: halogen, $CF_3$, $OCF_3$, OH, linear or branched $C_1$-$C_4$ alkyl; a saturated eterocycle with at least 4 carbon atoms and at least 1 heteroatom; $C_3$-$C_8$ cycloalkyl in turn optionally substituted with one or more of the following groups: linear or branched $C_1$-$C_4$ alkyl, $CF_3$ or OH;
$SR_5$, $SO_2R_5$ or $COR_5$ wherein $R_5$ is linear or branched $C_1$-$C_6$ alkyl; otherwise Ar is an eterocycle ring selected from the group of thiophene, benzothiophene, dibenzothiophene, thianthrene, pyrrole, pyrazole, furan, benzofuran, dibenzofuran, indole, isoindole, benzofurane, imidazole, benzoimidazole, oxazole, isoxazole, benzoxazole, thiazole, pyridine, pyrimidine, pyrazine, pyridazine, quinoline, isoquinoline, quinazoline, quinoxaline, cinnoline, pyrazole, pyran, benzopyran, pyrrolizine, phtalazine, 1,5-naphthyridine, 1,3-dioxole, 1,3-benzodioxole, optionally substituted with one or more groups $R_3$ as defined above;

pharmaceutically acceptable salts and esters thereof.

A first group of preferred compounds is that in which: R and $R_1$ form a 3 carbon atoms ring with the carbon atom to which they are linked;

$R_2$ is fluorine;

G is COOR", wherein R" is H, linear or branched $C_1$-$C_4$ alkyl, $C_3$-$C_6$ cycloalkyl or ascorbyl;

Ar is phenyl as defined above.

A second group of preferred compounds is that in which:

R and $R_1$ form a 3 carbon atoms ring with the carbon atom to which they are linked;

$R_2$ is fluorine;

G is $CONH_2$ or $CONHSO_2R'''$ wherein R''' is linear or branched $C_1$-$C_4$ alkyl or $C_3$-$C_6$ cycloalkyl;

Ar is phenyl as defined above.

A third group of preferred compounds is that in which:

both R and $R_1$ are methyl;

$R_2$ is fluorine;

G is COOR" wherein R" is as defined above;

Ar is phenyl as defined above.

A fourth group of preferred compounds is that in which:

both R and $R_1$ are methyl;

$R_2$ is fluorine;

G is $CONH_2$ or $CONHSO_2R'''$, wherein R''' is as defined above;

Ar is phenyl as defined above.

A fifth group of preferred compounds is that in which:

R and $R_1$ form a 3 carbon atoms ring with the carbon atom to which they are linked;

$R_2$ is fluorine;

G is COOR" wherein R" is as defined above;

Ar is a heterocycle as defined above.

A sixth group of preferred compounds is that in which:

both R and $R_1$ are methyl;

$R_2$ is fluorine;

G is COOR" wherein R" is as defined above;

Ar is a heterocycle as defined above.

Particularly preferred are the following compounds:
2-methyl-2-(2-fluoro-4'-trifluoromethylbiphen-4-yl)propionic acid (CHF 4810);
2-methyl-2-(2-fluoro-4'cyclohexyl biphen-4-yl)propionic acid (CHF 4961);
1-(2-fluoro-4'-trifluoromethylbiphenyl-4-yl)cyclopropanecarboxylic acid (CHF 5022);
1-(4'-cyclohexyl-2-fluorobiphenyl-4-yl)cyclopropanecarboxylic acid (CHF 5023);
1-(4'-benzyloxy-2-fluorobiphenyl-4-yl)cyclopropanecarboxylic acid (CHF 5042);
1-(2-fluoro-4'-isopropyloxybiphenyl-4-yl)cyclopropanecarboxylic acid (CHF 5044);
1-(2-fluoro-3'-trifluoromethoxybiphenyl-4-yl)cyclopropanecarboxylic acid (CHF 5045);
1-(2-fluoro-4'-trifluoromethoxybiphenyl-4-yl)cyclopropanecarboxylic acid (CHF 5046);
1-(2-fluoro-3'-trifluoromethylbiphenyl-4-yl)cyclopropanecarboxylic acid (CHF 5058);
1-(4'-cyclopentyl-2-fluorobiphenyl-4-yl)cyclopropanecarboxylic acid (CHF 5059);
1-(4'-cycloheptyl-2-fluorobiphenyl-4-yl)cyclopropanecarboxylic acid (CHF 5060);

1-(2'-cyclohexyl-2-fluorobiphenyl-4-yl)cyclopropanecarboxylic acid (CHF 5061);
1-(2-fluoro-4'-hydroxybiphenyl-4-yl)cyclopropanecarboxylic acid (CHF 5070);
1-[2-fluoro-4'-(tetrahydropyran-4-yloxy)biphenyl-4-yl]-cyclopropanecarboxylic acid (CHF 5071);
1-(2,3',4'-trifluorobiphenyl-4-yl)cyclopropanecarboxylic acid (CHF 5073);
1-(3',4'-dichloro-2-fluorobiphenyl-4-yl)cyclopropanecarboxylic acid (CHF 5074);
1-(3',5'-dichloro-2-fluorobiphenyl-4-yl)cyclopropanecarboxylic acid (CHF 5075);
1-(3'-chloro-2,4'-difluorobiphenyl-4-yl)cyclopropanecarboxylic acid (CHF 5076);
1-(4-benzo[b]thiophen-3-yl-3-fluorophenyl)cyclopropanecarboxylic acid (CHF 5077);
1-(2-fluoro-4'-prop-2-inyloxy-biphenyl-4-yl)-cyclopropanecarboxylic acid (CHF 5078);
1-(4'-cyclohexyloxy-2-fluoro-biphenyl-4-yl)-cyclopropanecarboxylic acid (CHF 5079);
1-[2-fluoro-4'-(tetrahydropyran-4-yl)-biphenyl-4-yl]-cyclopropanecarboxylic acid (CHF 5080);
1-[2-fluoro-4'-(4-oxo-cyclohexyl)-biphenyl-4-yl]-cyclopropanecarboxylic acid (CHF 5081);
2-(2''-fluoro-4-hydroxy-[1,1':4',1'']tert-phenyl-4''-yl)-cyclopropanecarboxylic acid (CHF 5083);
1-[4'-(4,4-dimethylcyclohexyl)-2-fluoro[1,1'-biphenyl]-4-yl]-cyclopropanecarboxylic acid (CHF 5084);
1-[2-fluoro-4'-[[4-(trifluoromethyl)benzoyl]ammino][1,1'-biphenyl]-4-yl]-cyclopropanecarboxylic acid (CHF 5094);
1-[2-fluoro-4'-[[4-(trifluoromethyl)cyclohexyl]oxy][1,1'-biphenyl]-4-yl]-cyclopropanecarboxylic acid (CHF 5096);
1-[2-fluoro-4'-[(3,3,5,5-tetramethylcyclohexyl)oxy][1,1'-biphenyl]-4-yl]-cyclopropanecarboxylic acid (CHF 5102);
1-[4'-[(4,4-dimethylcyclohexyl)oxy]-2-fluoro[1,1'-biphenyl]-4-yl]-cyclopropanecarboxylic acid (CHF 5103);
1-(2,3',4''-trifluoro[1,1':4',1''-tert-phenyl]-4-yl)-cyclopropanecarboxylic acid (CHF 5104);
1-(2,2',4''-trifluoro[1,1':4',1''-tert-phenyl]-4-yl)-cyclopropanecarboxylic acid (CHF 5105);
1-(2,3'-difluoro-4''-hydroxy[1,1':4',1''-tert-phenyl]-4-yl)-cyclopropanecarboxylic acid (CHF 5106);
1-(2,2'-difluoro-4''-hydroxy[1,1':4',1''-tert-phenyl]-4-yl)-cyclopropanecarboxylic acid (CHF 5107);
2-(2-fluoro-3',5'-bis(chloro)biphen-4-yl)propionic acid amide (CHF 5125).

A more preferred group of compounds is that in which R and $R_1$ form a 3 carbon atoms ring with the carbon atom to which they are linked;
$R_2$ is fluorine;
G is COOH;
Ar is phenyl substituted with one or more groups in such a way as that the log P (the partition coefficient between n-octanol and water) of the whole molecule is equal or higher than 4.5 as calculated in silico by using the software QikProp® release version 2.1 (Schrodinger Inc).

It has indeed been found that the higher the log P of the molecule, the greater is the inhibition potency of the release of $A\beta_{42}$ peptide and that particularly potent compounds are those whose log P is equal or higher than 4.5, preferably higher than 5.0.

Examples of these compounds are CHF 5022, CHF 5074, CHF 5096, CHF 5105, CHF 5106 and CHF 5107.

The invention also relates to the pharmaceutically acceptable salts and esters prepared in order to increase the crossing of the hemato-encephalic barrier.

A further object of the present invention are the compounds of formula (I) as medicaments, in particular the use thereof in the preparation of pharmaceutical compositions for the treatment and/or the prevention of neurodegenerative diseases such as Alzheimer's disease.

Still a further object of the invention are solid or liquid pharmaceutical compositions, preferably for the oral use, comprising at least one compound of formula (I) in admixture with pharmaceutically acceptable excipients and/or carriers, for example those described in Remington's Pharmaceutical Sciences Handbook, XVII Ed., Mack Pub., N.Y., U.S.A.

The compounds of general formula (I) wherein R'' is H can be prepared according to methods of literature by palladium-catalyzed reaction between an aryl halide of formula (II)

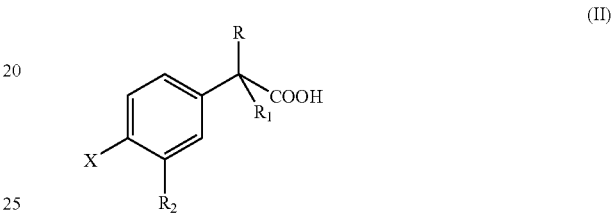

in which R, $R_1$ and $R_2$ are as defined above and X is bromine or iodine, preferably iodine, with a boronic acid or ester $ArB(OL)_2$ in which L is an alkyl chain, under the conditions reported in Scheme 1.

Scheme 1

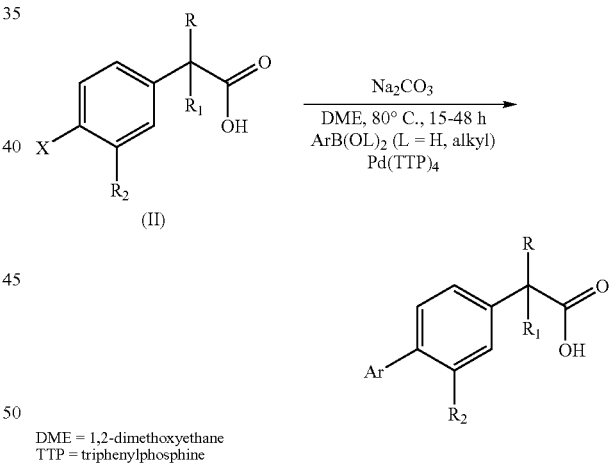

DME = 1,2-dimethoxyethane
TTP = triphenylphosphine

The compounds of formula (II) are commercially available, or can be prepared according to the following synthetic routes.

Derivatives in which R and $R_1$ are Straight or Branched $C_1$-$C_4$ alkyl (IIa).

Said compounds can be prepared according to the synthetic route shown in Scheme 2, starting from the arylacetic acids of formula (III) in which R and $R_2$ are as defined above and X is bromine or iodine.

The acid of formula (III) is esterified, alkylated, and optionally hydrolysed if the group G in the final product is COOH.

Scheme 2

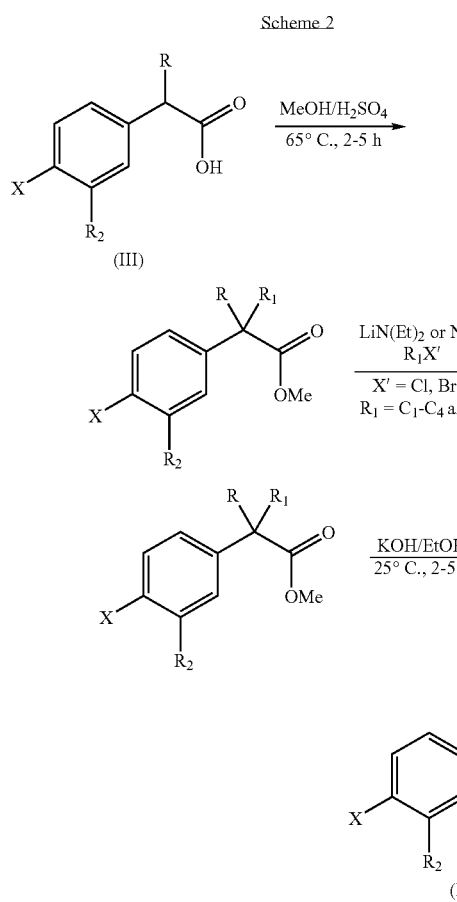

Derivatives in which R and R$_1$ Form a 3-6 Carbon Ring with the Carbon Atom to which They are Linked (IIb)

Said compounds are either commercially available, or can be prepared according to the synthetic route reported in Scheme 3 in which n is an integer of 1 to 4.

Scheme 3

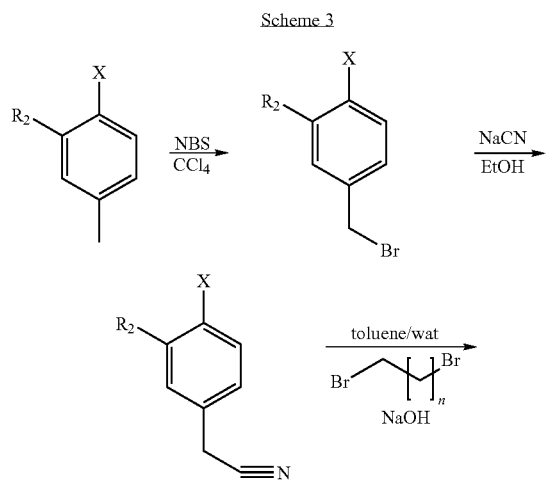

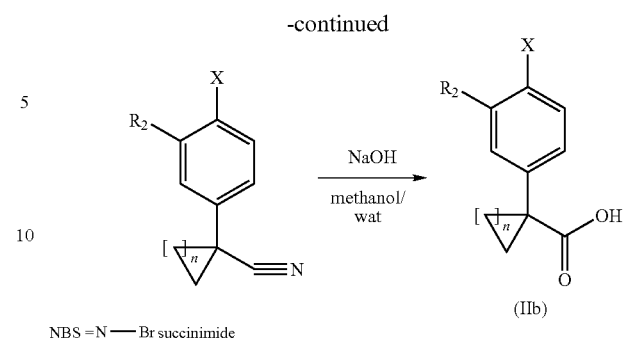

NBS = N—Br succinimide

Boronic acids or the corresponding boronates are either commercially available or can be prepared from the corresponding halide according to methods known in literature.

The compounds of formula (I) wherein G is COOR'', where R'' is linear or branched C$_1$-C$_4$ alkyl, C$_3$-C$_6$ cycloalkyl or ascorbyl, can be prepared by esterifying the compounds of formula (I) in which G is COOH.

The compounds of formula (I) in which G is CONH$_2$ or CONHSO$_2$R''' where R''' is linear or branched C$_1$-C$_4$ alkyl or C$_3$-C$_6$ cycloalkyl can be prepared by reaction of the corresponding esters with NH$_3$ or the amine NH$_2$SO$_2$R'''.

The compounds of formula (I) in which G is tetrazolyl can be prepared from compounds of formula (I) according to known methods, for example transforming the carboxylic acid into amide, dehydrating the amide to nitrile and reacting the latter with tributyltin azide.

EXAMPLES

Examples of Chemical Preparation

Example 1

Preparation 2-methyl-2-(2-fluoro-4'-trifluoromethyl-biphen-4-yl)propionic acid (CHF 4810)

Preparation of methyl[2-(2-fluoro-4'-trifluoromethyl-biphen-4-yl)]propionate

A solution of 2-(2-fluoro-4'-trifluoromethylbiphenyl-4-yl) propionic acid (0.2 g, 0.64 mmoles) in methanol (3 ml) is added with 98% sulfuric acid (0.5 g) and refluxed for 2.5 hours. The solvent is removed under vacuum, the residue is taken up with ethyl acetate (5 ml) and washed with a 5% NaHCO$_3$ solution (5 ml), then with water. The solution is dried over Na$_2$SO$_4$ and concentrated under vacuum to afford an oil (0.2 g, 95%).

HPLC-UV purity (215 nm): 99%

Preparation of methyl[2-methyl-2-(2-fluoro-4'-trifluoromethylbiphen-4-yl)]propionate A solution of methyl[2-(2-fluoro-4'-trifluoromethylbiphen-4-yl)]propionate (0.2 g, 0.61 mmoles) in anhydrous THF (3 ml) at 0° C. and under nitrogen atmosphere, is added with 60% NaH (30 mg, 0.75 mmoles). The mixture is stirred for 30 minutes and added with CH$_3$I (70 μl, 0.91 mmoles). After 3 h the mixture is concentrated under vacuum and taken up with ethyl acetate (5 ml). The resulting solution is washed with a 5% NaHCO$_3$ solution (5 ml), then with water, dried over $Na_2SO_4$, concentrated under vacuum to give an oil (0.18 g, 87%) which is used for the subsequent reaction without further purification.

Preparation of 2-methyl-2-(2-fluoro-4'-trifluoromethylbiphen-4-yl)propionic acid A solution of methyl[2-methyl-2-(2-fluoro-4'-trifluoromethylbiphen-4-yl)]propionate (0.18 g, 0.53 mmoles) in ethanol (5 ml) is added with KOH (60 mg, 1 mmol) and kept under stirring for 3 h at room temperature. The mixture is diluted with $H_2O$ (5 ml) and the solution is washed with ethyl ether (5 ml). The organic phase is discarded. The aqueous phase is acidified to pH=2 with HCl, then extracted with ethyl acetate (10 ml). The organic phase is dried over $Na_2SO_4$ and concentrated under vacuum to give a white solid, which is purified by flash chromatography on $SiO_2$ (eluent hexane/ethyl acetate 8/2 v/v) to obtain the product as a white solid (16 mg, 10%).

HPLC-UV purity (215 nm): 97%.

$^1$H NMR (DMSO-d6): 12.56 (s br, 1H); 7.84 (d, 2H); 7.78 (d, 2H); 7.57 (dd, 1H); 7.32 (s, 1H); 7.29 (m, 1H); 1.52 (s, 6H);

MS (EI): 326 m/z (M+.), 281, 253.

Following the same procedure and using the suitable reactive, compound, CHF 4961 was prepared.

Example 2

Preparation of 1-(2-fluorobiphenyl-4-yl)cyclopropanecarboxylic acid (CHF 5041)

Preparation of 4-bromo-3-fluorobenzyl bromide

A solution of 4-bromo-3-fluorotoluene (10 g, 0.053 moles) in carbon tetrachloride (100 ml) is added with N-bromosuccinimide, (NBS; 14 g, 0.08 moles). The mixture is refluxed, added with dibenzoyl peroxide (100 mg, 0.4 mmoles), refluxed for 1 hour, then cooled at room temperature and extracted with water. The aqueous phase is discarded, the organic phase is washed with brine, dried over sodium sulfate and concentrated under vacuum to give an oil (16 g) which is subjected to chromatography on a silica gel column (150 g), eluting with hexane, to afford the product.

Preparation of 4-bromo-3-fluorophenylacetonitrile

A solution of 4-bromo-3-fluorobenzyl bromide (12.2 g, 0.03 moles) in ethanol (100 ml) is added with NaCN (2 g, 0.04 moles) and refluxed for 2 hours. The mixture is concentrated under vacuum; the resulting residue is taken up with water, then extracted with ethyl acetate. The organic phase is washed with brine, dried over sodium sulfate and concentrated under vacuum to give a dark oil (10 g), which is subjected to chromatography on a silica gel column (150 g), eluting with hexane:ethyl ether 7:3, to afford the product in the solid form.

Preparation of 4-bromo-3-fluorophenylcycloproyanenitrile

A solution of 4-bromo-3-fluorophenylacetonitrile (5 g, 23 mmoles) in toluene (20 ml) is added with 35 mmoles of 1,2-dibromoethane, a 50% NaOH aqueous solution (20 ml) and tetrabutylammonium bromide (1.6 g, 5 mmoles). The mixture is kept under stirring at room temperature for 5-12 hours, then diluted with water and extracted with ethyl acetate. The organic phase is washed with 1N HCl, then with brine, finally dried and concentrated under vacuum to give a brown solid, which is subjected to chromatography on a silica gel column (200 g), eluting with hexane-ethyl ether 1-1, to afford the product in the solid form.

Preparation of 4-bromo-3-fluorophenylcyclopropanecarboxylic acid

A suspension of 4-bromo-3-fluorophenylcyclopropanenitrile (21 mmoles) in methanol (10 ml) is added with a 35% NaOH aqueous solution (40 ml) and a 35% $H_2O_2$ aqueous solution (3 ml), then is refluxed for 4 hours, cooled at room temperature and added with 2N HCl (250 ml). The precipitated solid is collected by filtration and redissolved in a 5% $NaHCO_3$ aqueous solution (300 ml). The insoluble fraction is filtered off and the clear filtrate is acidified to pH=2 with 2N HCl. The product precipitates as a white solid, which is recovered by filtration and dried under vacuum.

Preparation of 1-(2-fluorobiphenyl-4-yl)cyclopropanecarboxylic acid 800 mg (3.1 mmoles) of 4-bromo-3-fluorophenylcyclopropanecarboxylic acid and 650 mg (3.4 mmoles) of phenylboronic acid are suspended in 8 ml of a 2M $K_2CO_3$ aqueous solution. The mixture is added with tetrabutylammonium bromide (960 mg, 3 mmoles) and palladium(II) acetate (40 mg, 0.18 mmoles) and heated at 130° C. in a closed reactor for 30 minutes. After cooling at room temperature, the mixture is added with 2M HCl (25 ml) and extracted with ethyl acetate. The organic phase is washed with 1N HCl, then with brine, finally dried and concentrated under vacuum to give an oil (1.7 g), which is crystallized from isopropyl ether-hexane to afford the product as a white solid (0.2 g).

HPLC (215 nm) 98%.

MS (EI; TSQ 700; parameters 180 C; 70 V; 200 uA): 256 (M+.); 210; 196.

$^1$H-NMR (DMSO): 12.41 (s br, 1H); 7.56-7.35 (m, 6H); 7.27 (m, 1H); 7.24 (s, 1H); 1.48 (m, 2H); 1.22 (m, 2H).

Following the same procedure as described in Example 1, starting from the suitable 4-bromophenylcycloalkanecarboxylic acids and using the appropriate reactives, compounds CHF 5022, CHF 5023 CHF 5042, CHF 5045, CHF 5046, CHF 5058, CHF 5059, CHF 5060, CHF 5061, CHF 5070, CHF 5071, CHF 5073, CHF 5074, CHF 5075, CHF 5076, CHF 5077, CHF 5078, CHF 5079, CHF 5080, CHF 5081, CHF 5083, CHF 5084, CHF 5094, CHF 5096, CHF 5102, CHF 5103, CHF 5104, CHF 5105, CHF 5106, CHF 5107 and CHF 5002 were prepared.

Example 3

Pharmacological Activity

Inhibition of $A\beta_{42}$ Release in the Supernatant of H4-15x Cells

H4-15x cells (human neuroglioma cells transfected with the human gene encoding for the precursor of β-amyloid protein APP695) were cultured in flasks (in incubator at 37° C., under aqueous vapour saturated atmosphere with 5% carbon dioxide), in the presence of hygromycin and blasticidin, which maintain the selective pressure for the cells continuously expressing the gene of interest.

When the cells reached about 90% confluency, they were collected and re-seeded in 24 wells plates (2×10⁵ cells each), in 0.5 ml of complete culture medium. After approx. 24 hours, when the cells had adhered to the well surface and reached confluency, the medium of each well was replaced with 0.5 ml of fresh culture medium, supplemented with a compound (I) to 100 micromolar final concentration. Each tested concentration was repeated in triplicate. The molecules used for the treatment were previously dissolved in dimethylsulfoxide (DMSO) or in a dimethylsulfoxide/water mixture, the final concentration of DMSO in the wells not exceeding 1%. Thus the prepared plates were incubated again overnight (14-16 hours); afterwards the cell supernatant was taken from each well and $A\beta_{42}$ and $A\beta_{40}$ proteins were quantitated. The assay was carried out with an instrumentation for microplates chemoluminescence analysis, which allows to separately quantify the two proteins and is based on the immobilization of an analyte-antibody complex on paramagnetic microbeads. One of the antibodies of this complex is marked with a ruthenium compound which, upon electrochemical excitement, gives a light signal, having intensity proportional to the amount of analyte present.

Inhibition of cyclooxygenase-1 (COX-1) in Rat Whole Blood

Whole blood was taken from the rat abdominal aorta and immediately placed in heparinized tubes. Aliquots of heparinized blood (500 μl) were preincubated with 100 μM concentration of the tested compounds or with the only carrier (DMSO) for 1 h at 37° C. Eicosanoid production was induced by addition of calcium ionophore A23187 (final concentration $5\times10^{-5}$ M) and was interrupted after 30 minute incubation by quickly placing the samples in dry ice. Thereafter, samples were centrifuged (12000 g×3 minutes a 4° C.) and the production of $TxB_2$ thromboxane B2 was calculated by radioimmunoassay.

The results expressed as percent inhibition of $A\beta_{42}$ release at 100 μM and percent COX-1 inhibitory activity at the same concentration are reported in Table 1. Flurbiprofen used as comparison at the same concentration showed approx. 25% inhibition of $A\beta_{42}$ release and 100% COX-1 inhibitory activity.

TABLE 1

Percent inhibition of $A\beta_{42}$ release and percent COX-1 inhibitory activity of representative compounds of the invention at 100 μM concentration.

| Compound | % inhibition of $A\beta_{42}$ release | % COX-1 inhibitory activity |
|---|---|---|
| CHF 4961 | 76.6 | 5.2 |
| CHF 4810 | 58.0 | — |
| CHF 5022 | 55.4 | 0.0 |
| CHF 5045 | 56.4 | 8.3 |
| CHF 5046 | 70.4 | 2.6 |
| CHF 5058 | 54.8 | 0.0 |
| CHF 5070 | 22.4 | 0.0 |
| CHF 5071 | 28.1 | 0.4 |
| CHF 5073 | 67.4 | 4.8 |
| CHF 5074 | 79.2 | 0.5 |
| CHF 5076 | 71.4 | 5.5 |
| CHF 5078 | 57.5 | 3.6 |
| CHF 5080 | 51.8 | 0.3 |
| CHF 5081 | 52.3 | 6.1 |
| CHF 5083 | 81.1 | — |
| CHF 5096 | 70.0 | 0.8 |
| CHF 5105 | 90.7 | 1.9 |
| CHF 5106 | 79.9 | 0.0 |
| CHF 5107 | 83.3 | 1.1 |

The invention claimed is:

1. A compound of formula (I):

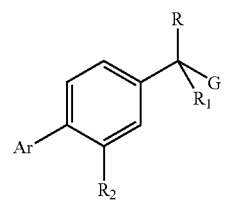

wherein:
R and $R_1$ together with the carbon atom to which they are linked form a ring which contains 3 to 6 carbon atoms;
G is a —COOH group;
$R_2$ is H or a halogen selected from the group consisting of F, Cl, Br, and I;
Ar is a group of formula

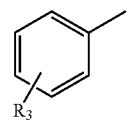

wherein $R_3$ represents one or more groups independently selected from:
a halogen selected from the group consisting of F, Cl, Br, and I;
$CF_3$;
$C_3$-$C_8$ cycloalkyl optionally substituted with one or more $C_1$-$C_4$ alkyl groups, oxo groups, or a combination thereof;
phenyl optionally substituted with one or more of the following groups:
halogen;
$CF_3$;
$OCF_3$;
OH;
a linear or a branched $C_1$-$C_4$ alkyl;
a saturated heterocycle with at least 4 carbon atoms and at least 1 heteroatom;
a $C_3$-$C_8$ cycloalkyl in turn optionally substituted with one or more of the following groups: a linear or a branched $C_1$-$C_4$ alkyl, $CF_3$ or OH;
$OR_4$ or $NHCOR_4$, wherein $R_4$ is $CF_3$, a linear or a branched $C_2$-$C_6$ alkenyl or alkynyl; a benzyl; a phenyl optionally substituted with one or more of the following groups: halogen, $CF_3$, $OCF_3$, OH, a linear or a branched $C_1$-$C_4$ alkyl;
a saturated heterocycle with at least 4 carbon atoms and at least 1 heteroatom;
a $C_3$-$C_8$ cycloalkyl in turn optionally substituted with one or more of the following groups: a linear or a branched $C_1$-$C_4$ alkyl, $CF_3$ or OH;
otherwise Ar is a heterocyclic ring, which may optionally be substituted with one or more $R_3$ groups, selected from the group consisting of thiophene, benzothiophene, dibenzothiophene;
or a pharmaceutically acceptable salt thereof.

2. A compound or pharmaceutically acceptable salt according to claim 1, wherein $R_2$ is fluorine.

3. A compound or pharmaceutically acceptable salt according to claim 1, wherein $R_2$ is fluorine; and Ar is phenyl substituted with one or more groups independently selected from:
- a halogen selected from the group consisting of F, Cl, Br, and I;
- $CF_3$;
- $C_3$-$C_8$ cycloalkyl optionally substituted with one or more $C_1$-$C_4$ alkyl groups, oxo groups, or a combination thereof;
- phenyl optionally substituted with one or more of the following groups: optionally substituted with one or more of the following groups:
- halogen;
- $CF_3$;
- $OCF_3$;
- OH;
- a linear or a branched $C_1$-$C_4$ alkyl;
- a saturated heterocycle with at least 4 carbon atoms and at least 1 heteroatom;
- a $C_3$-$C_8$ cycloalkyl in turn optionally substituted with one or more of the following groups: a linear or a branched $C_1$-$C_4$ alkyl, $CF_3$ or OH;
- $OR_4$ or $NHCOR_4$, wherein $R_4$ is $CF_3$, a linear or a branched $C_2$-$C_6$ alkenyl or alkynyl; a benzyl; a phenyl halogen, $CF_3$, $OCF_3$, OH, a linear or a branched $C_1$-$C_4$ alkyl;
- a saturated heterocycle with at least 4 carbon atoms and at least 1 heteroatom;
- a $C_3$-$C_8$ cycloalkyl in turn optionally substituted with one or more of the following groups: a linear or a branched $C_1$-$C_4$ alkyl, $CF_3$ or OH.

4. A compound or pharmaceutically acceptable salt according to claim 1, wherein $R_2$ is fluorine; and Ar is phenyl.

5. A compound or pharmaceutically acceptable salt according to claim 1, wherein $R_2$ is fluorine; and Ar is phenyl substituted with an optionally substituted phenyl.

6. A compound or pharmaceutically acceptable salt according to claim 1, wherein $R_2$ is fluorine; and Ar is an substituted or a substituted heterocyclic ring selected from the group consisting of thiophene, benzothiophene, and dibenzothiophene.

7. A compound or pharmaceutically acceptable salt according to claim 1, wherein $R_2$ is fluorine; Ar is phenyl substituted with one or more groups in such a way as that the log P of the whole molecule is equal or higher than 4.5 as calculated in silico by using the software QikProp® release version 2.1; Schrodinger Inc.

8. A compound or pharmaceutically acceptable salt according to claim 1, which is selected from the group consisting of
- 1-(2-fluoro-4'-trifluoromethylbiphenyl-4-yl)cyclopropanecarboxylic acid;
- 1-(3',4'-dichloro-2-fluorobiphenyl-4-yl)cyclopropanecarboxylic acid;
- 1-[2-fluoro-4'-(4-trifluoromethyl-cyclohexyloxy)-biphenyl-4-yl]-cyclopropanecarboxylic acid;
- 1-(2,2',4"-trifluoro[1,1';4',1"]terphenyl-4-yl)cyclopropanecarboxylic acid;
- 1-(2',2"-difluoro-4-hydroxy[1,1';4',1"]terphenyl-4"-yl)cyclopropanecarboxylic acid;
- 1-(2,2"-difluoro-4"-hydroxy[1,1';4',1"]terphenyl-4-yl)cyclopropanecarboxylic acid; and
- pharmaceutically acceptable salts thereof.

9. A pharmaceutical composition, comprising a compound or pharmaceutically acceptable salt according to of claim 1 and a pharmaceutically acceptable carrier, an excipient, or a combination thereof.

10. A pharmaceutical composition as claimed in claim 9, which is in a form suitable for oral administration.

11. A method of decreasing the production of neurotoxic peptide $A\beta_{42}$ in a subject suffering from Alzheimer's disease, comprising administering a compound or pharmaceutically acceptable salt according to claim 1 to said subject.

12. A method of treating Alzheimer's disease, comprising administering a composition according to claim 9 to a subject having Alzheimer's disease.

13. A method of treating Alzheimer's disease, comprising administering a compound or pharmaceutically acceptable salt according to claim 1, to a subject having Alzheimer's disease.

14. A pharmaceutical composition, comprising a compound or pharmaceutically acceptable salt according to claim 2 and a pharmaceutically acceptable carrier.

15. A pharmaceutical composition, comprising a compound or pharmaceutically acceptable salt according to claim 3 and a pharmaceutically acceptable carrier.

16. A pharmaceutical composition, comprising a compound or pharmaceutically acceptable salt according to claim 4 and a pharmaceutically acceptable carrier.

17. A pharmaceutical composition, comprising compound or pharmaceutically acceptable salt according to claim 6 and a pharmaceutically acceptable carrier.

18. A pharmaceutical composition, comprising a compound or pharmaceutically acceptable salt according to claim 5 and a pharmaceutically acceptable carrier.

19. A compound or pharmaceutically acceptable salt according to claim 1, which is selected from the group consisting of
- 1-(2-fluoro-4'-trifluoromethylbiphenyl-4-yl)cyclopropanecarboxylic acid;
- 1-(2-fluoro-3'-trifluoromethoxybiphenyl-4-yl)cyclopropanecarboxylic acid;
- 1-(2-fluoro-4'-trifluoromethoxybiphenyl-4-yl)cyclopropanecarboxylic acid;
- 1-(2-fluoro-3'-trifluoromethylbiphenyl-4-yl)-cyclopropanecarboxylic acid;
- 1-[2-fluoro-4'-(tetrahydro-pyran-4-yloxy)-biphenyl-4-yl]-cyclopropanecarboxylic acid;
- 1-(2,3',4'-trifluorobiphenyl-4-yl)cyclopropanecarboxylic acid;
- 1-(3',4'-dichloro-2-fluorobiphenyl-4-yl)cyclopropanecarboxylic acid;
- 1-(3'-chloro-2,4'-difluorobiphenyl-4-yl)cyclopropanecarboxylic acid;
- 1-[2-fluoro-4'-(4-oxo-cyclohexyl)-biphenyl-4-yl]-cyclopropanecarboxylic acid;
- 2-(2"-fluoro-4-hydroxy-[1,1';4',1']terphenyl-4"-yl)-propionic acid;
- 1-(2,2',4"-trifluoro[1,1';4',1"]terphenyl-4-yl)cyclopropanecarboxylic acid;
- 1-(2',2"-difluoro-4-hydroxy[1,1';4',1"]terphenyl-4"-yl)cyclopropanecarboxylic acid;
- 1-(2,2'-difluoro-4"-hydroxy[1,1';4",1"]terphenyl-4-yl)cyclopropanecarboxylic acid;

and
pharmaceutically acceptable salts thereof.

20. A compound or pharmaceutically acceptable salt according to claim 1, which is 1-(2-fluoro-4'-trifluoromethylbiphenyl-4-yl)cyclopropanecarboxylic acid or a pharmaceutically acceptable salt thereof.

21. A compound or pharmaceutically acceptable salt according to claim 1, which is 1-(3',4'-dichloro-2-fluorobiphenyl-4-yl)cyclopropanecarboxylic acid or a pharmaceutically acceptable salt thereof.

22. A compound or pharmaceutically acceptable salt according to claim 1, which is 1-[2-fluoro-4'-(4-trifluoromethyl-cyclohexyloxy)-biphenyl-4-yl]-cyclopropanecarboxylic acid or a pharmaceutically acceptable salt thereof.

23. A compound or pharmaceutically acceptable salt according to claim 1, which is 1-(2,2',4"-trifluoro[1,1';4',1"]terphenyl-4-yl)cyclopropanecarboxylic acid or a pharmaceutically acceptable salt thereof.

24. A compound or pharmaceutically acceptable salt according to claim 1, which is 1-(2',2"-difluoro-4-hydroxy[1,1';4',1"]terphenyl-4"-yl)cyclopropanecarboxylic acid or a pharmaceutically acceptable salt thereof.

25. A compound or pharmaceutically acceptable salt according to claim 1, which is 1-(2,2'-difluoro-4"-hydroxy[1,1';4',1"]terphenyl-4-yl)cyclopropanecarboxylic acid or a pharmaceutically acceptable salt thereof.

26. A compound or pharmaceutically acceptable salt according to claim 1, wherein R and $R_1$ together with the carbon atom to which they are linked form a ring which contains 3 carbon atoms.

* * * * *